United States Patent [19]

Grabowski et al.

[11] Patent Number: 5,326,586

[45] Date of Patent: Jul. 5, 1994

[54] COATING OF DRUG FORMS

[75] Inventors: Sven Grabowski; Kurt Wendel, both of Ludwigshafen; Astrid Kah-Helbig, Neustadt, all of Fed. Rep. of Germany

[73] Assignee: BASF Aktiengesellschaft, Ludwigshafen, Fed. Rep. of Germany

[21] Appl. No.: 957,375

[22] Filed: Oct. 7, 1992

[30] Foreign Application Priority Data

Oct. 7, 1991 [DE] Fed. Rep. of Germany ....... 4133192

[51] Int. Cl.$^5$ ................................................. A61K 9/00
[52] U.S. Cl. ................................. 427/487; 424/468; 424/480
[58] Field of Search ................. 427/3, 212; 424/418, 424/468, 479, 480; 526/238.22

[56] References Cited

U.S. PATENT DOCUMENTS

| | | | |
|---|---|---|---|
| 3,095,391 | 6/1963 | Brockway et al. | 526/238.22 |
| 4,060,506 | 11/1977 | Verbanac | 260/17.4 GC |
| 4,061,610 | 12/1977 | Glowaky et al. | 524/53 |
| 4,079,025 | 3/1978 | Young et al. | 526/238.22 |
| 4,112,215 | 9/1978 | Boessler et al. | |
| 4,115,332 | 9/1978 | Young et al. | 526/238.22 |
| 4,171,407 | 10/1979 | Elser et al. | 524/42 |
| 4,285,983 | 8/1981 | Saldarini et al. | 427/3 |
| 4,433,076 | 2/1984 | Bauer et al. | |
| 4,520,172 | 5/1985 | Lehmann et al. | |
| 4,663,163 | 5/1987 | Hou et al. | 210/656 |
| 4,704,295 | 11/1987 | Porter et al. | 427/3 |
| 4,737,357 | 4/1988 | Lehmann et al. | |
| 4,828,841 | 5/1989 | Porter et al. | 427/3 |
| 5,057,321 | 10/1991 | Edgren et al. | 424/473 |
| 5,116,890 | 5/1992 | Floyd et al. | 524/51 |
| 5,147,907 | 9/1992 | Rinck et al. | 524/48 |
| 5,248,516 | 9/1993 | Wheatley et al. | 427/3 |

FOREIGN PATENT DOCUMENTS 0408099 1/1991 European Pat. Off. .
1393374 5/1975 United Kingdom .

OTHER PUBLICATIONS

Biomaterials, vol. 11, No. 5, Jul. 5, 1990, pp. 345–349, J. Heller, et al., "Coating of Drug Forms".

Primary Examiner—Shrive Beck
Assistant Examiner—Diana Dudash
Attorney, Agent, or Firm—Oblon, Spivak, McClelland, Maier & Neustadt

[57] ABSTRACT

A process for coating drug forms by application of an aqueous dispersion which contains as binder a redispersed latex of an emulsion polymer onto the drug form and evaporating the water at a temperature at which the latex particles form a film, comprises employing a polymer dispersion which has been prepared by emulsion polymerization of one part by weight of at least one ethylenically unsaturated polymerizable monomer, by means of initiators which provide free radicals, in the presence of from 0.1 to 2 parts by weight of saccharified starch, and from 0 to 5% by weight, based on the monomer or monomers, of a surfactant, with or without further conventional additives, drying to a powder and redispersing in water.

1 Claim, 2 Drawing Sheets

Release of active substance from matrix tablets (Example 1) by USP XXII, Method 2

- • 0.1 N HCl
- ○ Buffer pH 7.4
- × pH change

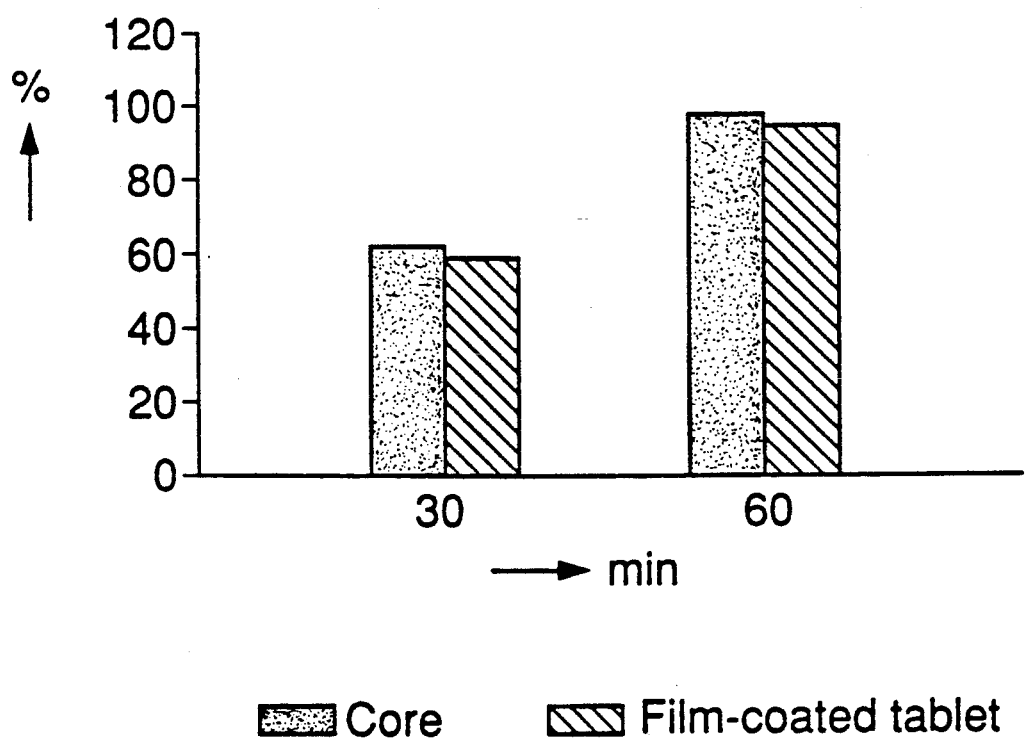

COATING OF DRUG FORMS

FIELD OF THE INVENTION

The present invention relates to a process for coating drug forms with a coating agent which is dispersible in water, and to the powdered, redispersible coating agent.

PRIOR ART

DE-C 21 35 073 describes the coating of drug forms using an aqueous dispersion of a polymer produced from vinyl monomers, from 10 to 55% by weight of which have a carboxyl or amino group. Coating with aqueous dispersions of coating agents has the advantage, compared with the use of organic solutions of coating agents, that the risk of fire and environmental pollution associated with organic solvents is avoided, but has the disadvantage that the preparation of the aqueous coating dispersions is difficult and cannot be done by the drug manufacturer. He is therefore obliged to purchase and store the binder together with the water. By contrast, he is able to prepare organic solutions from the powdered coating agent himself without difficulty.

According to DE-C 25 12 238, although it is possible to convert aqueous dispersions of binders for drug coatings into a powder by spray-drying, this must be dissolved in an organic solvent for use.

DE-A 30 49 179 describes the production of drug coatings from a spray-dried emulsion polymer powder by suspending it in an aqueous solution of an involatile plasticizer and applying the suspension to drug forms and heating it, which causes some of the water to evaporate and the suspended coating agent powder to dissolve in the plasticizer. This solution coalesces to a coating layer and solidifies on cooling. This process is called thermogelling. The film-forming process differs essentially from that of true aqueous lattices. In that case the cohesive pressure between the latex particles on gradual evaporation of the water is crucial, i.e. the latex particles are transformed directly as such into the coherent film, not via the intermediate stage of a solution.

The thermogelling process does not always meet all the requirements to be met by a coating process for drug forms and by the coating agents employed for this purpose. Since the coating agent powder is not redispersed as a latex but is suspended in larger particles, the resulting suspension often cannot be stored for a sufficient time. To obtain smooth and completely pore-free coatings, considerable amounts of plasticizer and high gelling temperatures must be used, otherwise the resulting coatings are rough and more or less porous, or it is necessary to apply very thick layers.

DE-A 34 38 291 describes a process for the preparation of an aqueous coating dispersion and the use thereof for coating drugs. A powdered copolymer which is swellable, but not soluble, in water and is composed of from 5 to 20% by weight of a monoethylenically unsaturated quaternary ammonium compound which can undergo free-radical polymerization, and of 95 to 70% by weight of at least one non-ionic, water-insoluble homopolymerforming comonomer can be dispersed in water at elevated temperature (from 50° to 100° C., preferably 60° to 80° C.) on stirring for at least 15 minutes. Pharmaceutical coatings or films with a diffusion permeability independent of the pH of the surrounding medium can be prepared from this dispersion.

The corresponding commercial product, a terpolymer of methyl methacrylate, ethyl acrylate and trimethylammonioethyl methacrylate chloride, can be bought as granulated bulk polymer and, as described in DE-A 34 38 291, after milling to a fine powder be redispersed in water at elevated temperature with stirring, with or without the addition of plasticizers. However, this elaborate process is not generally carried out by a drug manufacturer.

By contrast, a redispersible dispersion powder which can be converted into an aqueous coating agent only shortly before use for coating drug forms together with the other additives is a great advantage. EP-C 88 951 describes a dry powder of this type, composed of an emulsion polymer of A) from 20 to 85% by weight of units of at least one alkyl ester of acrylic and/or methacrylic acid,
B) from 80 to 15% of units of at least one monomer which is capable of free-radical polymerization and of salt formation and
C) with or without up to 30% by weight, based on the total of A+B, of units of one or more other monomers which can undergo free-radical polymerization whose powder grains are composed of loosely aggregated fine particles.

This powder can be converted into a coating agent dispersion by introducing it into water and redispersing to the extent of at least 80% by weight to latex particles in the presence of an agent which is capable of salt formation with the monomer units B) in an amount such that, after reaction thereof with the monomer units B), a total of 10 to 12% by weight, based on the weight of the copolymer of these units, are in the salt form.

Depending on the acidic or basic nature of the salt-forming groups in the emulsion polymer, the resulting coatings are resistant to gastric fluid and soluble in intestinal fluid or soluble in gastric fluid. Coatings resistant to gastric fluid are obtained when the monomers of component B contain carboxyl or carboxylate groups. The coatings rapidly dissolve in the alkaline intestinal fluid when the contents of these groups are high, while they dissolve more slowly or become diffusion permeable due to swelling when the contents are lower. Amino-containing monomers make the coating soluble in gastric fluid at high contents, and swellable and diffusion permeable in gastric fluid at low contents.

Owing to the salt-forming monomer units which are necessary for the redispersion of the dispersion powder described above, the solubility or diffusion permeability of the coating depends on the pH. It is impossible to achieve by this process a film-former which is insoluble in water and in the digestive fluids (gastric and intestinal fluids), but is swellable and permeable, for coatings and/or matrix tablets, and which is able to control the release of the active substance pH-independently via the diffusion-controlling film thickness in accordance with pharmacokinetic and therapeutic requirements.

In addition, care must be taken that the monomer composition of the film former is chosen so that spray-drying or freeze-drying of the dispersion is possible and, moreover, the emulsion polymer can be stored in powder form not in the glassy state at room temperature. This is why the glass transition temperature of the copolymer must be above 25° C., preferably above 40° C.

However, the hardness and friability of the film increase with the glass transition temperature. Accordingly, plasticizers must be employed for producing the coating agent, but this reduces the glass transition temperature again.

SUMMARY OF THE INVENTION

It is an object of the present invention to combine the advantages of coating drug forms with a coating agent dispersion with those of the use of dry coating agent powders. The aim was to develop a process which does not require large quantities of plasticizer or high film-forming temperatures but forms smooth and pore-free coatings. It should be possible to redisperse without difficulty the dispersion powder (the dried emulsion polymer) without the addition of salt-forming agents or of plasticizers in cold water without lengthy stirring. In addition, it ought to be possible to store in particular the powder, but also its aqueous redispersion, for a lengthy time. The film resulting from this coating agent ought to allow pH-independent release of the active substance, the aim being, on the one hand, instant release from drug forms coated with the coating agent and, on the other hand, delayed release from matrix tablets obtained by wet granulation with the coating agent and subsequent tableting.

We have found that this object is achieved by the process of the present invention.

BRIEF DESCRIPTION OF THE FIGURES

FIG. 2 shows a graphical representation of the results of relase of active substance from taste-masked film-coating tablets by USP XXII, Method 2 of Example 3 below.

THE EMULSION POLYMER

Figure 1:
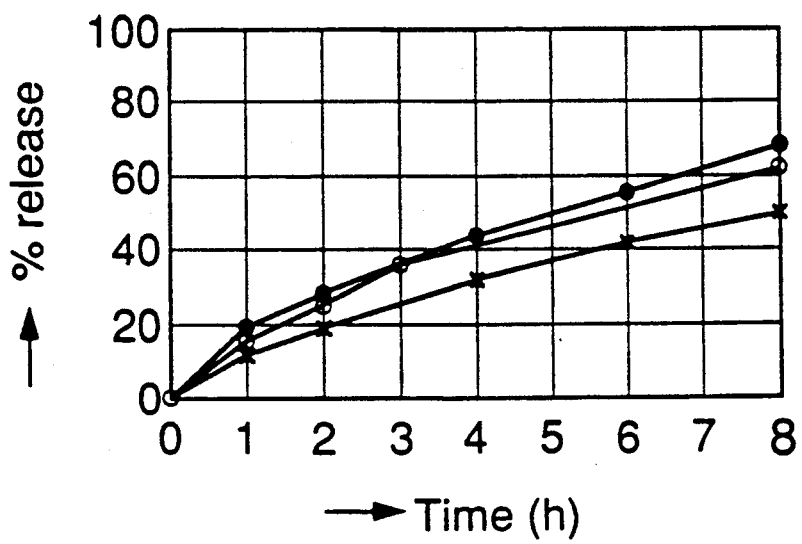
FIG. 1 shows a graphical representation of the results of release of active substance from matrix tablets by USP XXII, Method 2 of Example 1 below.

The object is achieved according to the present invention by starting from aqueous polymer dispersions which can be prepared by emulsion polymerization of ethylenically unsaturated compounds, using initiators providing free radicals, in the presence of saccharified starch of weight average molecular weight 2,500–25,000, with or without further conventional additives such as described in DE-A 39 22 784, at from 30 to 120, preferably 40° to 100° C.

Examples of suitable ethylenically unsaturated polymerizable monomers are (meth)acrylic esters of $C_1$–$C_{18}$-alcohols, such as methyl methacrylate and ethyl acrylate, also hydroxyalkyl esters of (meth)acrylic acid, vinyl esters and vinyllactams; furthermore unsaturated mono- or dicarboxylic acids such as (meth)acrylic acid, maleic, fumaric, crotonic and itaconic acid, and mono-esters or monoamides of these acids. Suitable monomers with amino groups are vinylimidazole, vinylimidazoline, vinylimidazolidine, vinylpyridine, monoalkyl- and dialkylaminoalkyl esters or monalkyl- or dialkylamino-alkylamides of unsaturated polymerizable carboxylic acid. It is likewise possible to employ anionic monomers such as salts of acrylamidoalkylsulfonic acids, cationic monomers such as trimethylammonioethyl methacrylate chloride, multifunctional crosslinking monomers such as methylol(meth)acrylamides and derivatives thereof.

The choice of the monomers or monomer mixtures and the ratio thereof to the amount of the starch derivative employed depends, on the one hand, on the requirements of the coating process (glass transition temperature, minimum film-forming temperature) and, on the other hand, on the required properties of the coating (solubility in various media, hardness, friability and elasticity of the film).

The amount of saccharified starch to be employed is from 10 to 200, preferably 20 to 50, % of the weight of the polymer. Saccharified starch is composed of the products which are obtained on hydrolysis of starch in aqueous phase and which have a weight average molecular weight of 2500–25000. They are commercially available (for example the C* PUR products 01906, 01908, 01910, 01912, 01915, 01921, 01924, 01932 or 01934 of Cerestar Deutschland GmbH, D-4150 Krefeld 12).

The preparation of saccharified starch is generally known and described, inter alia, in Günther Tegge, Stärke und Stärkederivate, Behr's Verlag, Hamburg 1984, pages 173 and 220 et seq., and in EP-A 441 197. Particularly suitable examples are the starch saccharification products which comply with the Guidelines for Starch and certain Starch Products (1975) of the Bund für Lebensmittelrecht und Lebensmittelkunde e.V. and which have the legal status of a foodstuff. The saccharified starches which are preferably used according to the invention are those whose weight average molecular weight $M_w$ is in the range from 4000 to 16000, particularly preferably in the range from 6500 to 13000.

The saccharified starches to be used according to the invention are normally completely soluble in water at room temperature, the solubility limit usually being above 50% by weight, which is a particular advantage for the preparation of the aqueous polymer dispersions according to the invention.

It has also proven beneficial for the saccharified starches to be used according to the invention to have a non-uniformity N (defined as the ratio of the weight average molecular weight $M_w$ to the number average molecular weight $M_n$; N characterizes the molecular weight distribution) in the range from 6 to 12. N is particularly advantageously from 7 to 11 and very particularly beneficially from 8 to 10.

It is furthermore advantageous for the content of the saccharified starches to be used according to the invention, which have a molecular weight below 1000, to be at least 10% by weight but not more than 70% by weight. The content is particularly preferably in the range from 20 to 40% by weight.

It is additionally advantageous to use saccharified starches whose dextrose equivalent DE is from 5 to 40, preferably from 10 to 30 and particularly preferably from 10 to 20. The DE characterizes the reduction capacity based on the capacity to reduce anhydrous dextrose and is determined by the DIN 10308 method, version 5.71 (compare also Günther Tegge, Stärke und Stärkederivate, Behr's Verlag, Hamburg 1984, p. 305).

It has also emerged that aqueous polymer dispersions with a particularly beneficial profile of properties are obtained when the saccharified starches have a dynamic viscosity $\eta^{40}$ [Pa.s], determined by the DIN 53 019 method on 40% by weight aqueous solutions at 25° C. with a shear rate of 75 $s^{-1}$, from 0.01 to 0.06, preferably from 0.0 15 to 0.04, and particularly preferably from 0.02 to 0.035.

It should be stated at this point that, unless indicated otherwise, data in the specification on the molecular weight of saccharified starches to be used according to the invention are based on determinations by gel permeation chromatography under the following conditions.

Columns: Three 7.5×600 mm steel columns packed with TSK gel G 2000 PW, G 3000 PW and G 4000 PW; pore width 5 μm
Eluent: Distilled water
Temp.: RT
Detection: Differential refractometer (eg. ERC 7511)
Flow rate: 0.8 ml/min. Pump: eg. ERC 64.00
Volume injected: 20 μl. Valve: eg. VICI 6-way valve
Evaluation: Bruker Chromstar GPC Software
Calibration: Glucose, raffinose, maltose and maltopentose for the low molecular weight range. Pullulan standards with a polydispersity <1.2 for the high molecular weight range.

Suitable starting materials for the preparation of the saccharified starches to be used according to the invention are in principle all natural starches such as cereal starches (e.g. corn, wheat, rice or millet), tuber and root starches (e.g. potatoes, tapioca or arrowroot) or sago starches.

An essential advantage of the saccharified starches to be used according to the invention is that, apart from the partial hydrolysis of the starch, which is extremely easy to carry out, they require no further chemical modification to prepare them for use. However, they can, of course, also be used according to the invention in chemically modified form, e.g. by etherification or esterification. This chemical modification can also be carried out on the starch before it is hydrolized. Esterification is possible both with inorganic and with organic acids, or the anhydrides or chlorides thereof. Phosphated and acetylated hydrolyzed starches are of particular interest. The most usual method for etherification is treatment with organic halides, epoxides or sulfates in aqueous alkaline solution. Particularly suitable ethers are alkyl ethers, hydroxyalkyl ethers, carboxyalkyl ethers and allyl ethers. Also suitable are products of the reaction with 2,3-epoxypropyltrimethylammonium chloride. Chemically unmodified saccharified starches are preferred.

Free radical-forming initiators which can be used are hydrogen peroxide, water-soluble organic peroxides and hydroperoxides, possibly combined with reducing compounds such as ascorbic acid, water-soluble azo compounds such as 2,2'-azobis(2-amidinopropane) dihydrochloride, and inorganic peroxides such as alkali metal or ammonium salts of peroxodisulfuric acid, in amounts of from 0.1 to 2, preferably 0.2 to 1, % of the total weight of the monomers.

If required, it is possible to add other conventional aids to the reaction mixture. These aids include nucleation lattices which improve the reproducibility of the particle size of the final products, buffer mixtures, complexing agents, dispersants and emulsifiers. The emulsion polymer is normally prepared in the presence of small amounts (about 0.1-5, preferably 0.5-1.5, % of the weight of the monomers) of anionic, cationic or non-ionic surfactants (emulsifiers) or compatible mixtures thereof in the form of an aqueous latex with a solids content of from 30 to 70% by weight. When obtaining the dry polymer powder from the latex, care must be taken that the latex particles are retained as such and do not form inseparable aggregates. This is possible by ensuring that the polymer is isolated below the minimum film-forming temperature. Particularly suitable processes are spray-drying and freeze-drying. The present invention does not relate to the preparation of the powdered emulsion polymer.

THE COATING AGENT AND ITS USE

The coating agent is composed of the powdered emulsion polymer in an aqueous redispersion which contains 0 to 5, preferably 0 to 1, % by weight of surfactant and has a solids content of from 10 to 60, preferably 20 to 45, % by weight. Besides the polymer, it contains from 0 to 90, preferably 20 to 70, % by weight, based on the total solids content, of conventional pharmaceutical aids such as pigments, lubricants such as magnesium stearate or talc, flavorings, sugars, polishing agents, plasticizers etc., which are normally dispersed separately in water and subsequently admixed, or incorporated directly into the redispersion. The binder content is from 10 to 100, preferably from 30 to 90, % of the total weight of solids. The solids content and viscosity of the coating agent depend on the application process. The viscosity is generally about 5–40 mPa.s. More conventional application processes can be used, e.g. conventional pan coating or the coating of drug forms in a fluidized bed.

The amount of coating agent usually applied to the drug surface is from 0.5 to 10 mg of solid per square centimeter, to result in film thicknesses of from 1 to 100 micron. The coating agent can, as in other coating processes, be applied a little at a time in several layers, between each of which drying is possible. It is likewise possible for the coating agent to be applied continuously and simultaneously dried with air at a slightly elevated temperature. It is generally sufficient for the surface of the drug form to be coated to be at no higher than about 40° C., usually below 35° C., preferably from 25° to 35° C., in which case the inlet air must be at from 40° to 70° C., depending on the evaporation rate and the apparatus design.

The film-forming component (the polymer) of the coating agent is called the binder, irrespective of whether it is used together with undissolved aids. Accordingly, the result of the film formation is, in the absence of undissolved additives, a more or less clear polymer coating or, in the presence of undissolved additives, a concealing coating. The film formation occurs directly from the latex state. The latex particles are present in their original form, although as loose aggregates. They can therefore be dispersed almost completely to single latex particles in a dispersion.

The binder for preparing an aqueous coating agent can be transported and stored as a dry powder, which saves space and weight and removes the risk of a loss of quality, until the coating agent is prepared. The redispersion requires neither lengthy stirring nor elevated temperatures nor the addition of salt-forming agents or plasticizers.

The small amount of surfactant required for the emulsion polymerization means that there is little foaming either of the primary dispersion or of the coating agent dispersion resulting from the redispersion of the powder. Nevertheless, it has adequate stability, for example to cold, heat and added electrolytes.

The redispersible powder to be employed according to the invention can be prepared either by freeze-drying or by spray-drying the emulsion polymer. It is also possible to prepare redispersible powders from copolymers which, when pure, have a glass transition temperature below 25° C. and a correspondingly, below room temperature, minimum film-forming temperature. No addition of spray aids in the spray-drying is necessary for this. The dispersion powder is stable on storage even without the addition of antiblocking agents.

Although the coating agent can also contain conventional plasticizers to adjust the required hardness and elasticity of the film, the amounts of these required are not such as to make the film soft and tacky during preparation, as during the formation of films from organic solvents or in thermogelling. Furthermore, it is possible surprisingly, to prepare not only a redispersible, storable powder but also, from this, non-tacky, elastic coatings with high ultimate tensile strength without the addition of plasticizers even from copolymers which are intrinsically very soft. This is a considerable advantage of the process according to the invention compared with the preparation of coatings from copolymers with glass transition temperatures which are sufficiently high for spray-drying (and correspondingly high minimum film-forming temperatures). It is also possible according to the invention, surprisingly, to prepare delayed release tablets in spite of the content of soluble saccharified starch.

APPLICATIONS

The solution properties of the resulting film can be controlled by the amount of saccharified starch employed in the emulsion polymerization. Since it is possible in principle, but not necessary, in contrast to EP-C 88 951 cited above, to employ monomer units containing ionizable groups, such as amino or carboxyl groups, in the copolymer to ensure redispersability, it is possible to prepare films with a diffusion permeability independent of the pH of the surrounding medium. Thus, it is possible after wet granulation with the dispersions according to the invention and subsequent tableting to produce matrix tablets which permit delayed release of the active substance. However, it is likewise possible to obtain coatings which disintegrate in a medium at a faster or slower rate and pH-independently by altering the content of saccharified starch in the dispersion.

By drug forms are meant all solid drug forms, e.g. uncoated and (film-)coated tablets or granules, but not powders.

EXAMPLES

Example 1

Production of Delayed Release Matrix Tablets 125 g of anhydrous theophylline of particle size from 0.2 to 0.7 mm were mixed with 75 g of calcium hydrogen phosphate, moistened with 20.8 g of water and granulated with 35.23 g of a polymer dispersion with a 30% solids content composed of ethyl acrylate and methyl methacrylate in the ratio 2:1 by weight, which had been prepared by emulsion polymerization in the presence of 20% by weight of maltodextrin, based on the total of the monomers. The granules were dried in a circulating air oven for 24 hours, screened and compressed to tablets with a diameter of 8 mm and a weight of 215 mg in a rotary machine with a force of 15 kN. Release of active substance from the tablets was pH-independent and delayed for 8 h (USP XXII, Method 2; FIG. 1).

EXAMPLE 2

Use as Rapidly Disintegrating Film Coating 1.5 g of Sicopharm quinoline yellow lacquer, 6.0 g of titanium dioxide and 7.5 g of talc were converted into a fine suspension in 107.5 g of water in an Ultra-Turrax. 125.0 g of an aqueous 30% strength polymer dispersion composed of ethyl acrylate and methyl methacrylate in the ratio 2:1 by weight, which had been prepared by emulsion polymerization in the presence of 30% by weight of maltodextrin, based on the total of the monomers, spray-drying and redispersing, were stirred into this suspension. 500 g of the resulting coating suspension were sprayed onto 2.5 kg of placebo cores in a fluidized bed, equivalent to an application rate of of 1.4 mg/cm$^2$, based on the polymer. The inlet air was at 42° C., and the spraying rate was about 20 g/min. The coated tablets were dried in a circulating air oven at 40° C. overnight. The coating provided a uniform cover and was smooth and shiny. The disintegration time of the tablets was virtually unaffected by the coating, being from 3 to 4 minutes.

EXAMPLE 3

Use as Taste-Masking Coating 500 g of a 40% strength spray suspension prepared as in Example 2 but employing only 20% of maltodextrin (in place of 30) in the emulsion polymerization were applied in an Accela-Cota (Manesty Machines Ltd., Speke, Liverpool L 249 LQ, UK) to 5 kg of theophylline-containing cores at a spray rate of about 20 g/rain with the inlet air at 50° C. The application rate was 0.7 mg/cm$^2$, based on the polymer. The taste of the coated tablets was masked for several minutes. There was no delay in the release of the active substance in vitro (USP XXII, Method 2, 0.1N HCl; FIG. 2).

We claim:

1. A process for coating drug forms by application of an aqueous dispersion which contains as binder a redispersed latex of a physiologically acceptable emulsion polymer onto the drug form and evaporating the water at a temperature at which the latex particles form a film, which comprises employing a polymer dispersion which has been prepared by emulsion polymerization of one part by weight of at least one ethylenically unsaturated polymerizable monomer, by means of initiators which provide free radicals, in the presence of from 0.1 to 2 parts by weight of saccharified starch of average molecular weight 2,500–25,000, and from 0 to 5% by weight, based on the monomer or monomers, of a surfactant, with or without further additives, drying to a powder and redispersing in water.

* * * * *